(12) United States Patent
Weast et al.

(10) Patent No.: US 9,983,565 B2
(45) Date of Patent: May 29, 2018

(54) TECHNOLOGIES FOR BIO-CHEMICALLY CONTROLLING OPERATION OF A MACHINE

(71) Applicant: Intel Corporation, Santa Clara, CA (US)

(72) Inventors: John C. Weast, Portland, OR (US); Brian D. Johnson, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 313 days.

(21) Appl. No.: 14/671,698

(22) Filed: Mar. 27, 2015

(65) Prior Publication Data

US 2016/0282842 A1   Sep. 29, 2016

(51) Int. Cl.
*G05D 7/00* (2006.01)
*G05B 19/406* (2006.01)

(52) U.S. Cl.
CPC .. *G05B 19/406* (2013.01); *G05B 2219/24162* (2013.01)

(58) Field of Classification Search
CPC .................................................... G05B 19/406
USPC ......................................................... 700/283
See application file for complete search history.

(56) References Cited

U.S. PATENT DOCUMENTS

| | | | | |
|---|---|---|---|---|
| 7,667,609 B1* | 2/2010 | Roe | ......................... | B60K 28/06 180/272 |
| 8,868,036 B1* | 10/2014 | Nasserbakht | ........... | H04M 3/16 455/410 |
| 9,104,886 B1* | 8/2015 | Dolbakian | .............. | G06F 21/62 |
| 9,231,765 B2* | 1/2016 | Flautner | ................ | H04L 9/3226 |
| 2003/0097307 A1* | 5/2003 | Greene | .................. | G06Q 20/20 705/26.1 |
| 2008/0147953 A1* | 6/2008 | Lawandus | ........... | H04L 63/0861 710/313 |
| 2010/0121315 A1 | 5/2010 | Trovato | | |
| 2010/0312188 A1 | 12/2010 | Robertson | | |
| 2011/0159463 A1* | 6/2011 | Samain | ................ | A45D 44/005 434/100 |

(Continued)

FOREIGN PATENT DOCUMENTS

| WO | 2014-092741 | 6/2014 |
|---|---|---|
| WO | 2014-151929 | 9/2014 |

OTHER PUBLICATIONS

International Search Report for PCT/US16/019805, dated Jul. 11, 2016 (4 pages).

(Continued)

*Primary Examiner* — Vincent Tran
(74) *Attorney, Agent, or Firm* — Barnes & Thornburg LLP (57) ABSTRACT

Technologies for bio-chemically controlling operation of a machine include applying a bio-chemical agent to an operator of the machine and controlling an operational characteristic of the machine based on the presence of the bio-chemical agent on the operator. The operational characteristic of the machine may be controlled based on the presence or lack of the biochemical agent on the operator. In some embodiments, the bio-chemical agent may be configured to generate a bio-chemical trigger in response to exposure to a biochemical or biological characteristic of the operator. The operation of the machine may be controlled based on such bio-chemical trigger or reaction.

22 Claims, 6 Drawing Sheets

(56) References Cited

U.S. PATENT DOCUMENTS

| | | | | |
|---|---|---|---|---|
| 2011/0228989 A1* | 9/2011 | Burton | ................... | G06F 21/32 |
| | | | | 382/116 |
| 2013/0200997 A1* | 8/2013 | Miller | ...................... | G05B 1/00 |
| | | | | 340/5.52 |
| 2013/0345290 A1* | 12/2013 | Erdmann | ............. | C12N 15/113 |
| | | | | 514/44 A |
| 2014/0106357 A1* | 4/2014 | Berrada | ................... | C12Q 1/68 |
| | | | | 435/6.12 |
| 2014/0181941 A1* | 6/2014 | Quint | ..................... | G06Q 10/06 |
| | | | | 726/7 |
| 2016/0035233 A1* | 2/2016 | Breed | ..................... | G09B 7/00 |
| | | | | 345/8 |
| 2016/0123941 A1* | 5/2016 | Bowers | .............. | G01N 33/0009 |
| | | | | 422/98 |

OTHER PUBLICATIONS

Written Opinion for PCT/US16/019805, dated Jul. 11, 2016 (7 pages).

\* cited by examiner

TECHNOLOGIES FOR BIO-CHEMICALLY CONTROLLING OPERATION OF A MACHINE

BACKGROUND

Many mechanical systems have various mechanical controls to control the user operation of the system. For example, manufacturing machines and systems may have mechanical switches and controls to ensure proper operation of the machine. Additionally, some systems may include security devices and systems to ensure that only an authorized operator is controlling the machine. Such security systems are often embodied as physical devices, such as keys, card readers, or passcode entry systems. However, other security systems may utilize static biological properties of the operator. For example, a handprint scanner or a retina scanner may analyze the corresponding biological properties of the user to authorize or deny the user access to the system.

Traditional mechanical operation control and security systems can provide some amount of assurance of proper machine operation by a user. However, such systems typically produce a binary pass/fail and do not continually validate that the user remains authorized to operate the system. Additionally, such typical systems are generally not customized to the operator, which may allow unauthorized operators to control the system through acquisition of identification devices (e.g., key, scan card, password, etc.).

BRIEF DESCRIPTION OF THE DRAWINGS

The concepts described herein are illustrated by way of example and not by way of limitation in the accompanying figures. For simplicity and clarity of illustration, elements illustrated in the figures are not necessarily drawn to scale. Where considered appropriate, reference labels have been repeated among the figures to indicate corresponding or analogous elements.

DETAILED DESCRIPTION OF THE DRAWINGS

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C): (A and B); (B and C); (A and C); or (A, B, and C). Similarly, items listed in the form of "at least one of A, B, or C" can mean (A); (B); (C): (A and B); (B and C); (A or C); or (A, B, and C).

The disclosed embodiments may be implemented, in some cases, in hardware, firmware, software, or any combination thereof. The disclosed embodiments may also be implemented as instructions carried by or stored on one or more transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Figure 1:
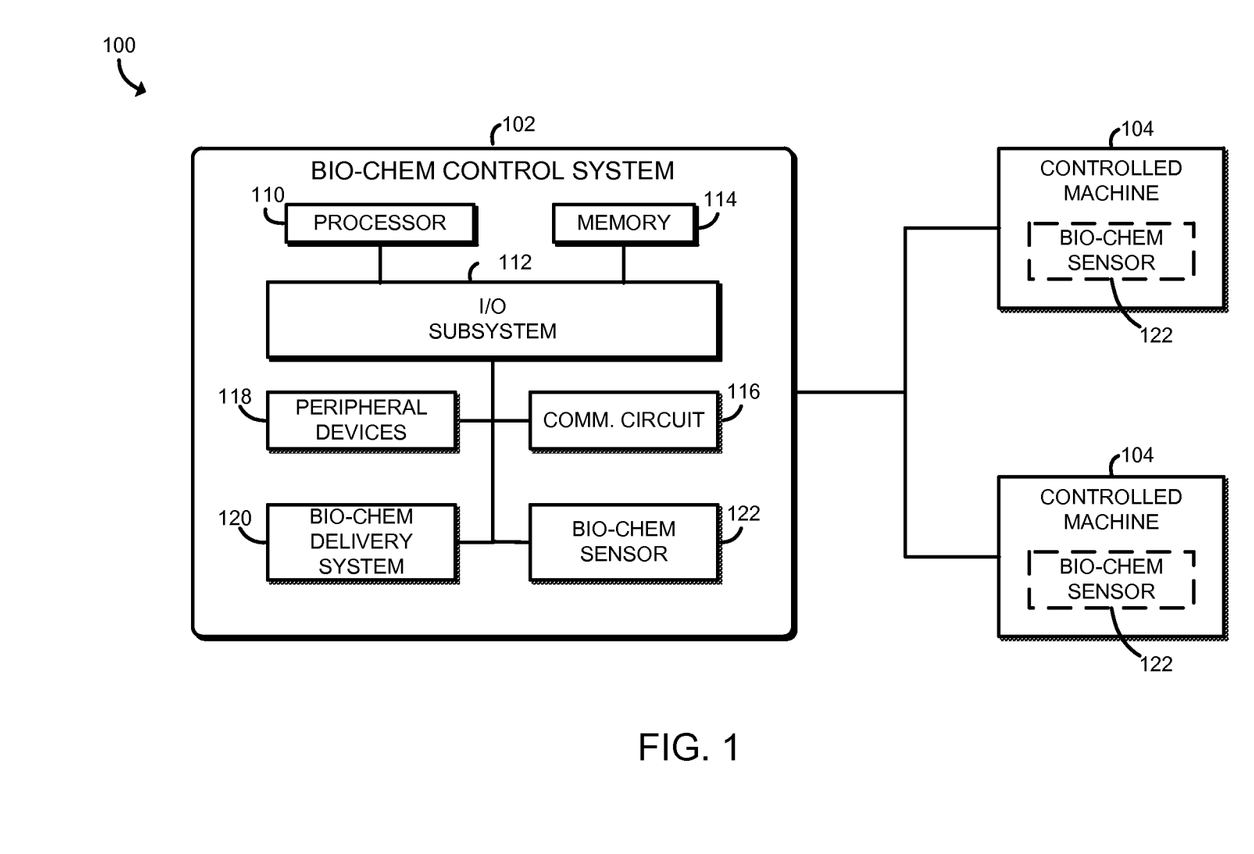
FIG. 1 is a simplified block diagram of at least one embodiment of a system for bio-chemically controlling operation of a machine.

Referring now to FIG. 1, a system 100 for bio-chemically controlling operation of a machine includes a bio-chemical control system 102 and one or more controlled machines 104. In use, the bio-chemical control system 102 is configured to dispense or deliver a bio-chemical agent to an operator of a controlled machine 104 and monitor the presence, lack thereof, and/or biological interactions of the bio-chemical agent with the operator to control access to and operation of the controlled machines 104. The bio-chemical agent may be embodied as any type of biological, chemical, or biological-chemical agent usable on an individual to perform the various functions described below. As such, as used herein, the term "bio-chemical" means biological, chemical, or biological-chemical. In some embodiments, the bio-chemical agent is customized to the operator. For example, the bio-chemical agent may be customized to a biological characteristic of the operator and, in some cases, may be only "active" for the technologies disclosed herein when applied to the corresponding operator. Additionally, as discussed in more detail below, the bio-chemical agent may be applied to the operator in various forms including, but not limited to, as a pill, a mist, an injection, a salve, a liquid, a spray, or other delivery mechanism.

As discussed in more detail below, the bio-chemical control system 102 is configured to control the operation of the controlled machines 104 based on a bio-chemical agent applied to the operator. For example, in an embodiment, the bio-chemical control system 102 senses for the applied bio-chemical agent to the operator and only authorizes operation of a controlled machine 104 if the bio-chemical agent is sensed on the operator. In this way, the bio-chemical control system 102 can control access to the controlled machine 104 by the proper operator and control how long the operator controls the machine (e.g., in embodiments in which the bio-chemical agent decays from the operator over time). In other embodiments, the bio-chemical agent may be used as a bio-chemical analysis tool to detect forbidden substances in an operator and/or detect operator fatigue as discussed in more detail below. Additionally, in some embodiments, the bio-chemical agent may be used as a personal signature by the operator to allow the bio-chemical control system 102 to customize or personalize a controlled machine 104 to that particular operator. Further, in some embodiments, the bio-chemical agent may be used to safely control operator behavior.

The bio-chemical control system 102 may be embodied as any type of computer, controller, or computing system capable of performing the functions described herein. For example, the bio-chemical control system 102 may be embodied as a computer, a controller, a server, a server controller, a distributed computing system, a multiprocessor system, a multi-computer system, a computerized machine, and/or other computing device capable of monitoring bio-chemical agents. It should be appreciated that although the bio-chemical control system 102 is illustrated in FIG. 1 as a single computing device, the bio-chemical control system 102 may be embodied as a collection or network individual computing devices in some embodiments.

As shown in FIG. 1, the bio-chemical control system 102 includes a processor 110, an I/O subsystem 112, memory 114, a communication circuit 116, one or more peripheral devices 118, a bio-chemical delivery system 120, and one or more bio-chemical sensors 122. Of course, the bio-chemical control system 102 may include other or additional components, such as those commonly found in a computer device (e.g., various input/output devices), in other embodiments. Additionally, in some embodiments, one or more of the illustrative components may be incorporated in, or otherwise from a portion of, another component. For example, the memory 114, or portions thereof, may be incorporated in the processor 110 in some embodiments.

The processor 110 may be embodied as any type of processor capable of performing the functions described herein. For example, the processor may be embodied as a single or multi-core processor(s), digital signal processor, microcontroller, or other processor or processing/controlling circuit. Similarly, the memory 114 may be embodied as any type of volatile or non-volatile memory or data storage capable of performing the functions described herein. In operation, the memory 114 may store various data and software used during operation of the bio-chemical control system 102 such as operating systems, applications, programs, libraries, and drivers. The memory 114 is communicatively coupled to the processor 110 via the I/O subsystem 112, which may be embodied as circuitry and/or components to facilitate input/output operations with the processor 110, the memory 114, and other components of the bio-chemical control system 102. For example, the I/O subsystem 112 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 112 may form a portion of a system-on-a-chip (SoC) and be incorporated, along with the processor 110, the memory 114, and other components of the bio-chemical control system 102, on a single integrated circuit chip.

The communication circuit 116 may be embodied as any communication circuit, device, or collection thereof, capable of enabling communications between the bio-chemical control system 102 and the controlled machines 104. To do so, the communication circuit 116 may be configured to use any one or more communication technology and associated protocols (e.g., Ethernet, Bluetooth®, Wi-Fi®, WiMAX, etc.) to effect such communication. In use, as discussed in more detail below, the bio-chemical control system 102 may control the operation of the controlled machines 104 via such communications, which may be wired or wireless.

The peripheral devices 118 may include any type of peripheral device commonly found in a typical computing device, such as various input/output devices. For example, the peripheral devices 118 may include display circuitry, various input buttons and switches, a keyboard, a mouse, speaker, microphone, and/or other peripheral devices.

The bio-chemical delivery system 120 may be embodied as any type of delivery system capable of applying the bio-chemical agent(s) to an operator. For example, the bio-chemical delivery system 120 may be embodied as a pill dispensing system, an auto-injection system, a mister or sprayer, or the like. In some embodiments, the bio-chemical delivery system 120 may be co-located with the controlled machines 104. In other embodiments, the bio-chemical delivery system 120 may be located remotely therefrom. For example, in some embodiments, the bio-chemical delivery system 120 may be located at an entrance to a facility housing the controlled machines 104 to ensure the bio-chemical agent is properly applied to each operator.

The bio-chemical sensor 122 may be embodied as any type sensor or collection of sensors capable of sensing various aspects of the bio-chemical agent. For example, the bio-chemical sensor 122 may be configured to sense the presence of the bio-chemical agent, the presence of an altered-state of the bio-chemical agent (e.g., in response to a biological trigger), and/or the presence of a reaction or interaction of the bio-chemical agent with biological features or characteristics of the operator (e.g., an illicit drug). In some embodiments, each of the controlled machines 104 may include one or more bio-chemical sensors located at the controlled machine to similarly sense the bio-chemical agent, altered-states of the bio-chemical agent, and/or reactions or interactions of the bio-chemical agent.

Each of the controlled machines 104 may be embodied as any type of machine, tool, computing device, vehicle, or other device. In the illustrative embodiment, the controlled machines 104 are embodied as manufacturing machines, but may be other types of machines, tools, or devices in other embodiments. For example, in some embodiments, the controlled machines 104 may be embodied as controlled vehicles (e.g., a tractor trailer, a forklift, etc.). Additionally, although the illustrative system 100 is shown as having only two controlled machines 104, the system 100 may include a greater or less number of controlled machines 104 in other embodiments. For example, the bio-chemical control system 102 may be configured to control an array of controlled machines 104 in some embodiments.

Figure 2:
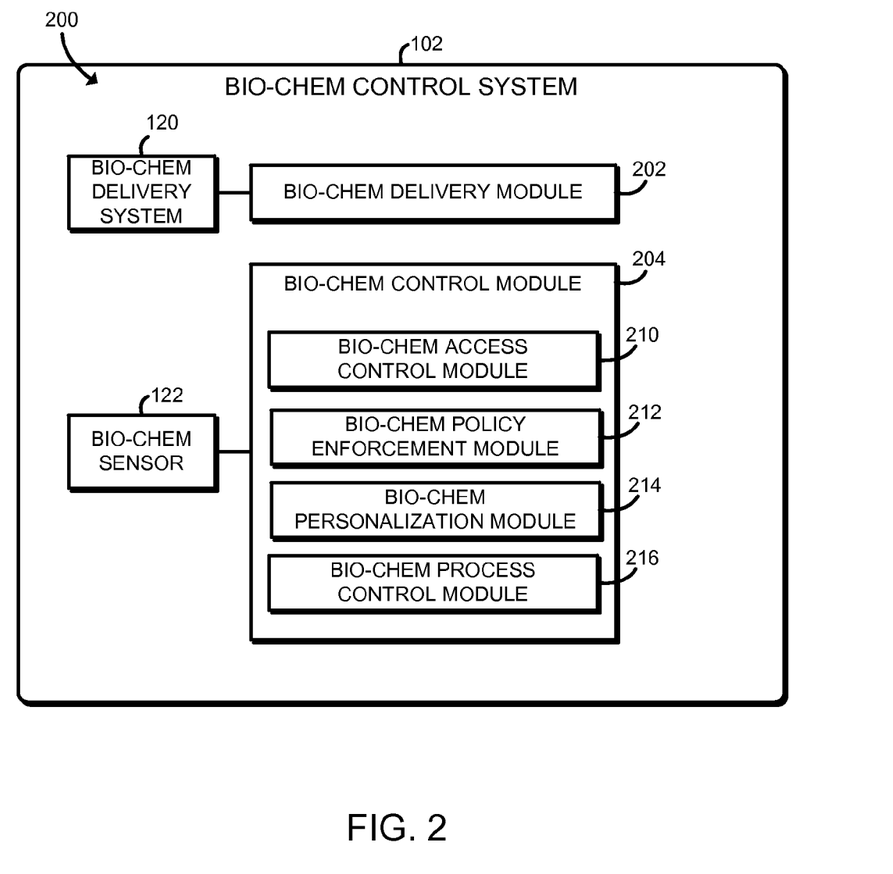
FIG. 2 is a simplified block diagram of at least one embodiment of an environment that may be established by a bio-chemical control system of the system of FIG. 1.

Referring now to FIG. 2, in use, the bio-chemical control system 102 may establish an environment 200. The illustrative environment 200 includes a bio-chemical delivery module 202 and a bio-chemical control module 204. Each of the modules and other components of the environment 200 may be embodied as firmware, software, hardware, or a combination thereof. For example the various modules, logic, and other components of the environment 200 may form a portion of, or otherwise be established by, the processor 110, the I/O subsystem 112, an SoC, or other hardware components of the bio-chemical control system 102. As such, in some embodiments, any one or more of the modules of the environment 200 may be embodied as a circuit or collection of electrical devices (e.g., bio-chemical delivery circuit and a bio-chemical control circuit, etc.).

The bio-chemical delivery module 202 is configured to control the operation of the bio-chemical delivery system 120 to apply the bio-chemical agent to the operator of a controlled machine 104. As discussed above, the bio-chemical delivery system 120 may be embodied as any type of delivery system capable of applying the bio-chemical agent(s) to the operator including, but not limited to a pill dispensing system, an auto-injection system, a mister or sprayer, or the like. As such, the bio-chemical delivery module 202 controls the dispensation of the bio-chemical agent to the operator. In some embodiments, the bio-chemical delivery module 202 may perform some amount of identification or security check to ensure the correct bio-chemical agent is applied to the correct operator. For example, the bio-chemical delivery module 202 may perform a biological match based on a biological sample of the operator in those embodiments in which the bio-chemical agent is customized to a biological characteristic (genome, DNA, etc.) of the operator.

The bio-chemical control module 204 is configured to control operation of the controlled machines 104 based on the presence and/or aspects of the bio-chemical agent applied to the operator. The bio-chemical control module 204 may be configured to control the controlled machines 104 in any suitable way based on the presence and/or aspects of the bio-chemical agent. To do so, for example, the bio-chemical control module 204 may include a bio-chemical access control module 210. The bio-chemical access control module 210 is configured to control access to a controlled machine 104 based on the presence of a bio-chemical agent on the operator. For example, if the operator does not have the bio-chemical agent present, the bio-chemical control system 102 may restrict operation of the controlled machine 104.

The bio-chemical control module 204 also includes a bio-chemical policy enforcement module 212. The bio-chemical policy enforcement module 212 is configured to control operation of the controlled machine 104 based on sensing a bio-chemical trigger caused by the bio-chemical agent. For example, the bio-chemical agent may be configured to generate the bio-chemical trigger (e.g., to transform or generate a different bio-chemical agent) in response to contact with another agent, such as an illicit drug or substance.

Additionally, the bio-chemical control module 204 also includes a bio-chemical personalization module 214. The bio-chemical personalization module 214 is configured to personalize or customize the operation of a controlled machine 104, a user interface of the controlled machine 104, or other aspect of the controlled machine 104 based on the presence of the bio-chemical agent on the operator. In such embodiments, the bio-chemical agent may act as a personal signature facilitating the customization of the controlled machine 104. For example, a different bio-chemical agent may be applied to each operator or the bio-chemical agent may be engineered to be modifiable based on an individual biological characteristics. In some embodiments, the same bio-chemical agent may be applied to each operator and is configured to generate a unique bio-chemical reaction or combination based on each operator's unique biological characteristics (e.g., genome, DNA, etc), which may act as a personalization key.

The bio-chemical control module 204 also includes a bio-chemical process control module 216. The bio-chemical process control module 216 is configured to enforce machine policies. To do so, the bio-chemical process control module 216 may be configured to dispense a reactant bio-chemical agent engineered to adversely react with the bio-chemical agent applied to the operator. Such reactions may cause, for example, irritation, stench, or other unpleasant effect to control the behavior of the operator. Further in some embodiments, the reaction may be engineered to temporarily incapacitate the operator (e.g., cause temporary blindness, paralysis, or worse) or otherwise significantly deter the operator (e.g., in those cases in which the "operator" is an un-authorized attacker, intruder, or combatant).

Figure 3:
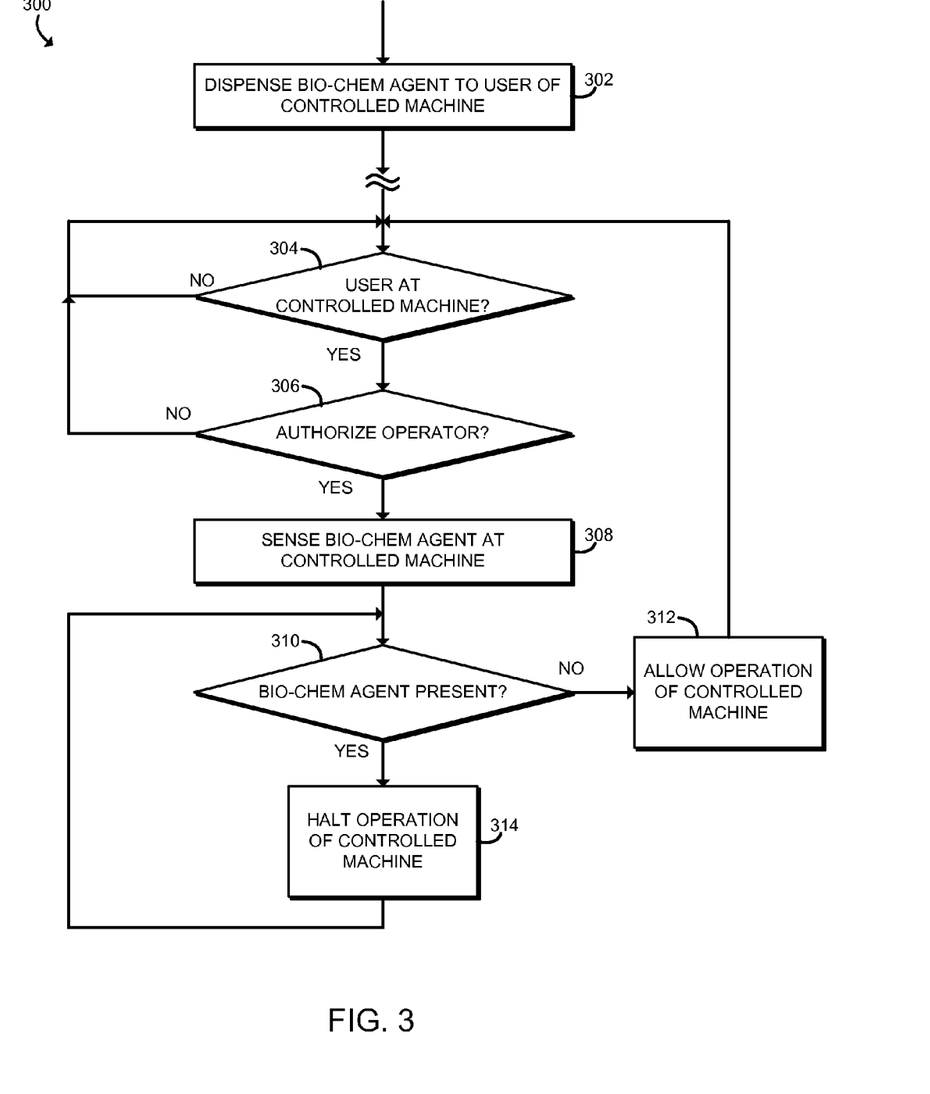
FIG. 3 is a simplified flow diagram of at least one embodiment of a method for controlling access to a machine based on a bio-chemical agent that may be executed by the bio-chemical control system of FIG. 2.

Referring now to FIG. 3, in use, the bio-chemical control system 102 may execute a method 300 for controlling access to a controlled machine 104. The method 300 begins with block 302 in which a bio-chemical agent is applied to the operator. As discussed above, the bio-agent may be applied at the controlled machine 104 or remotely therefrom (e.g., at an entrance to the facility). Additionally, in some embodiments, the bio-chemical agent may be applied prior to the expected operation of the controlled machine 104 (e.g., days prior).

Subsequently, in block 304, the bio-chemical control system 102 determines whether a user is located at the controlled machine 104. To do so, the bio-chemical control system 102 may utilize any suitable technology for detecting a person's presence at the controlled machine 104. For example, the controlled machine 104 may include pressure sensitive flooring, motion sensing, cameras or other sensor, or infer an operator's presence from interactions with the controlled machine 104. Regardless, if the bio-chemical control system 102 detects a person's presence at the controlled machine 104, the method 300 advances to block 306 in which the bio-chemical control system 102 determines whether to authorize the operator. That is, the bio-chemical control system 102 may authorize the user as a binary condition (e.g., at the initiation of the work cycle) or may continually or periodically authorize the operator.

If the bio-chemical control system 102 determines that operator authorization is required, the method 300 advances to block 308 in which the bio-chemical control system 102 monitors for the bio-chemical agent applied to the operator. For example, the bio-chemical sensor 122 may generate sensor data indicative of the presence of the bio-chemical agent on the operator (i.e., whether the bio-chemical agent is present or not). If the bio-chemical control system 102 detects the presence of the bio-chemical agent, the bio-chemical control system 102 allows the operator to operate the controlled machine 104 in block 312. If, however, the bio-chemical control system 102 determines that the bio-chemical agent is not present on the operator, the method 300 advances to block 314 in which the bio-chemical control system 102 halts operation of the controlled machine 104. For example, the bio-chemical control system 102 may turn the controlled machine 104 off or otherwise disallow control or operation of the controlled machine 104. In this way, the bio-chemical control system 102 controls access to the controlled machine 104 based on the presence of the bio-chemical agent. It should be appreciated that the method 300 may also be used to control the shift length of an operator. For example, the biochemical agent may be engineered to decay over time consistent with the length of a shift or allowed operation time for the operator. In such embodiments, the controlled machine 104 will turn off or otherwise become unusable even if the operator desires to continue working. For example, in embodiments in which a controlled machine 104 is embodied as a controlled vehicle, the vehicle may become inoperable to the operator thereby limiting the total time (e.g., drive time) the operator can operate the controlled vehicle (e.g., to require sleep time by the operator).

Figure 4:
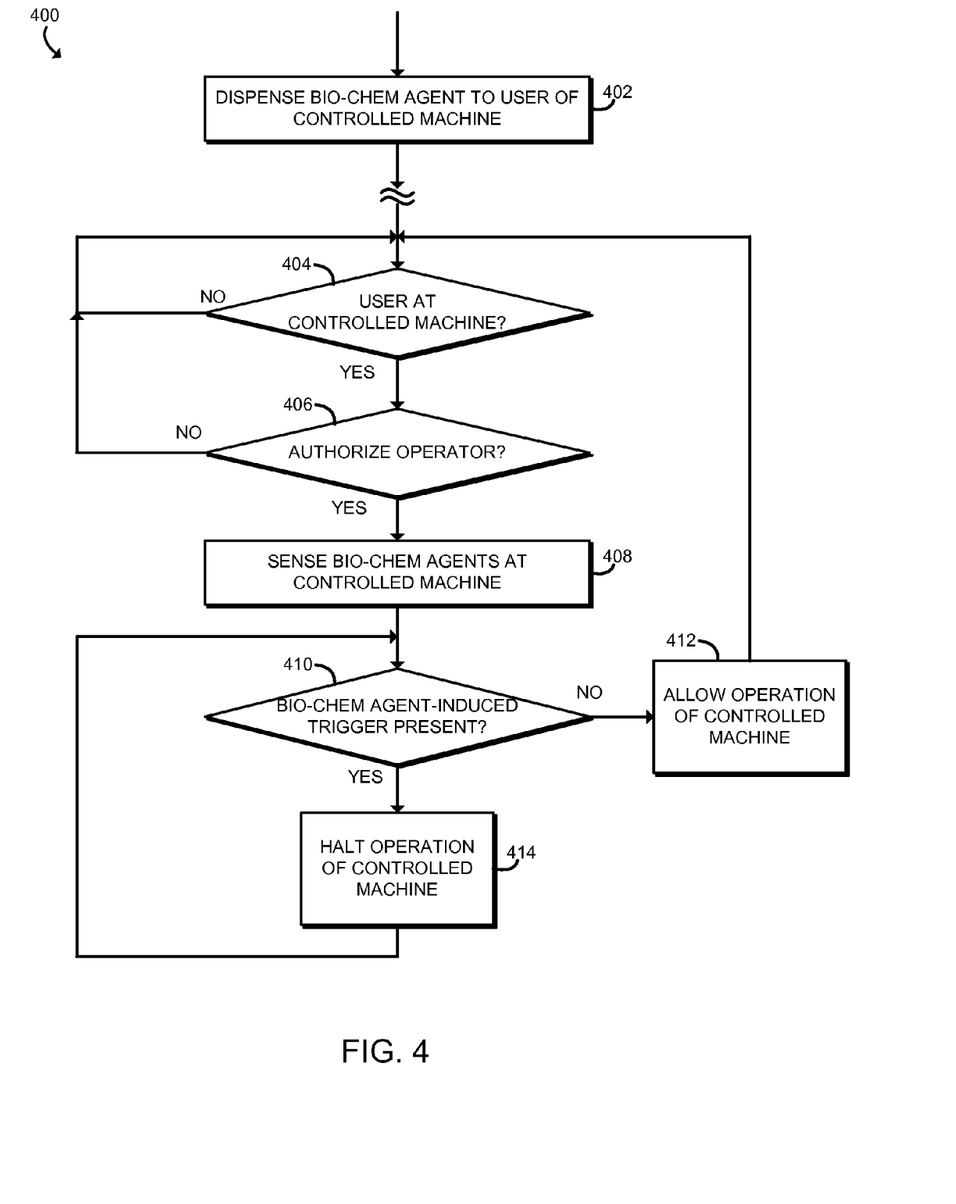
FIG. 4 is a simplified flow diagram of at least one embodiment of a method for enforcing operation policy of a machine based on a bio-chemical agent that may be executed by the bio-chemical control system of FIG. 2.

Referring now to FIG. 4, in use, the bio-chemical control system 102 may also execute a method 400 for enforcing an operation policy of a controlled machine 104. The method 400 begins with block 402 in which a bio-chemical agent is applied to the operator as discussed above. Subsequently, in block 404, the bio-chemical control system 102 determines whether a user is located at the controlled machine 104. If so, the method 400 advances to block 406 in which the bio-chemical control system 102 determines whether to authorize the operator. Again, the bio-chemical control system 102 may authorize the user as initially, continually, or periodically.

If the bio-chemical control system 102 determines that operator authorization is required, the method 400 advances to block 408 in which the bio-chemical control system 102 senses bio-chemical agents located at the controlled machine 104. In particular, in block 410, the bio-chemical control system 102 determines whether a bio-chemical agent-induced trigger is present at the controlled machine 104. As discussed above, the biochemical agent may be engineered to induce or generate a bio-chemical trigger in response to contact with a banned substance (e.g., a drug) or the like. The bio-chemical trigger may be embodied as any type of bio-chemical agent or substance detectable by the bio-chemical control system 102. For example, the bio-chemical agent may be engineered to be altered when it contacts a banned substance or to produce a secondary bio-chemical agent.

Additionally, in some embodiments, the bio-chemical agent may be engineered to generate the bio-chemical trigger in response to biological characteristics of the operator. For example, the biochemical agent may generate the bio-chemical trigger in response to the user becoming sleepy or having an emergency medical condition. In this way, the bio-chemical control system 102 may monitor for dangerous operator behavior or state and respond by controlling the monitored machine to provide safety to the operator.

Referring back to block 410, if the bio-chemical control system 102 does not detect the bio-chemical agent-induced trigger, the method 400 advances to block 412 in which the bio-chemical control system 102 allows the operator to continue operation of the controlled machine 104. If, however, the bio-chemical control system 102 determines that the bio-chemical agent-induced trigger is present, the method 400 advances to block 414 in which the bio-chemical control system 102 halts operation of the controlled machine 104.

Figure 5:
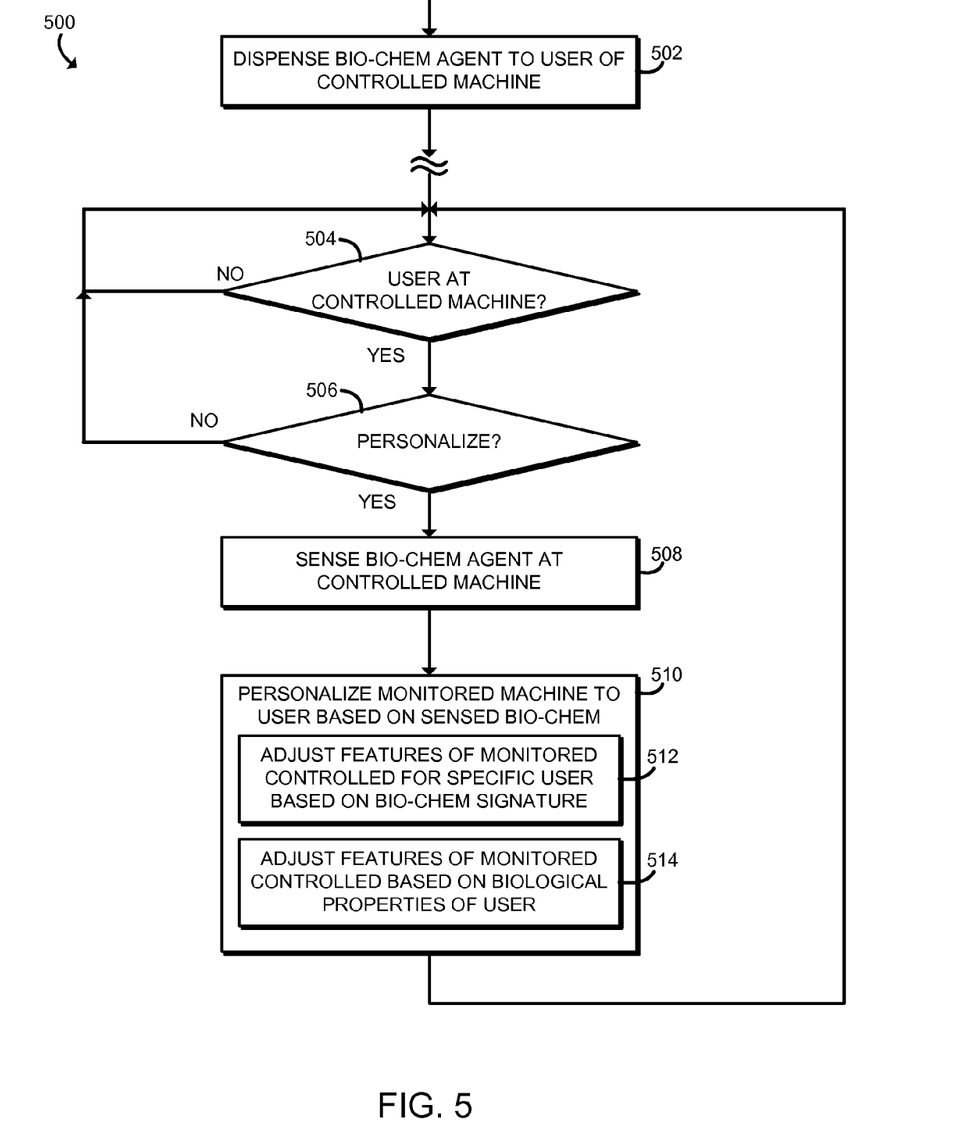
FIG. 5 is a simplified flow diagram of at least one embodiment of a method for personalizing machine operation based on a bio-chemical agent that may be executed by the bio-chemical control system of FIG. 2.

Referring now to FIG. 5, in use, the bio-chemical control system 102 may also execute a method 500 for personalizing the operation of a controlled machine 104 based on the bio-chemical agent. The method 400 begins with block 502 in which a bio-chemical agent is applied to the operator as discussed above. Subsequently, in block 504, the bio-chemical control system 102 determines whether a user is located at the controlled machine 104. If so, the method 500 advances to block 506 in which the bio-chemical control system 102 determines whether personalization of the operation of the controlled machine 104 is desired.

If personalization of the operation of the controlled machine 104 is desired, the method 500 advances to block 408 in which the bio-chemical control system 102 senses bio-chemical agent applied to the operator of the controlled machine 104. Subsequently, in block 510, the bio-chemical control system 106 personalizes the controlled machine 104 based on the sensed bio-chemical agent and/or unique bio-chemical reaction or combination of the operator to the bio-chemical agent. For example, in block 512, the bio-chemical control system 106 may adjust features of the controlled machine 104 for the specific operator based on the bio-chemical signature (i.e., based on the specific bio-chemical agent). In such embodiments, an operator may apply a specific bio-chemical agent to cause personalization of the controlled machine 104 based on the specific bio-chemical agent (which may also be used by another operator). Alternatively, in block 514, the operator may utilize a bio-chemical agent engineered to react with the biological characteristics of the operator to generate a unique bio-chemical agent signature for the operator. In either case, the bio-chemical control system 102 adjusts the features of the controlled machine 104 based on the bio-chemical agent or alterations thereof. To do so, the bio-chemical control system 102 may adjust or alter any feature of the controlled machine 104 such as, for example, a user interface, control locations, mechanical adjustments, and/or the like.

Figure 6:
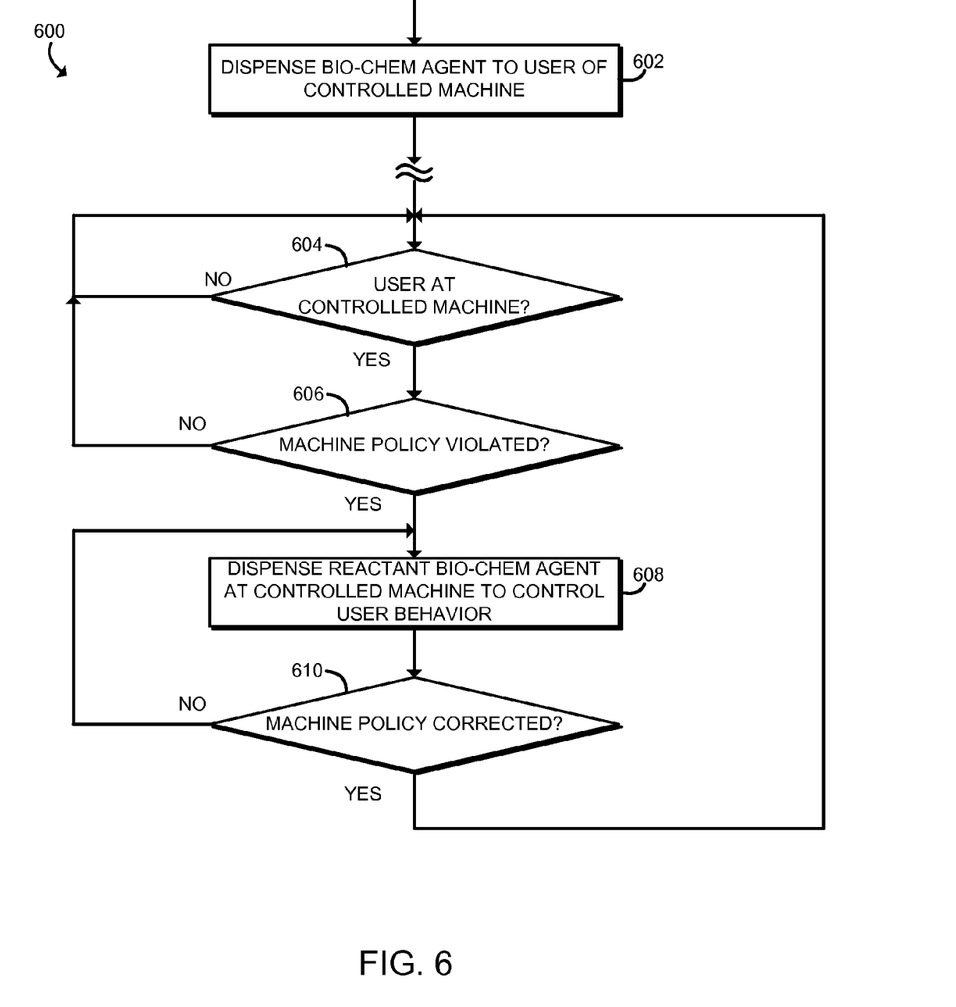
FIG. 6 is a simplified flow diagram of at least one embodiment of a method for enforcing a process control of a machine based on a bio-chemical agent that may be executed by the bio-chemical control system of FIG. 2.

Referring now to FIG. 6, in use, the bio-chemical control system 102 may additionally execute a method 600 for enforcing a process control on a controlled machine 104 based on the bio-chemical agent. The method 600 begins with block 602 in which a bio-chemical agent is applied to the operator as discussed above. Subsequently, in block 604, the bio-chemical control system 102 determines whether a user is located at the controlled machine 104.

If the bio-chemical control system 102 determines that a user or person is located at the controlled machine 104 in block 604, the method 600 advances to block 606 in which the bio-chemical control system 102 determines whether a control policy of the controlled machine 104 has been violated. The control policy may be embodied as any type of policy that dictates how the controlled machine 104 is to be operated. For example, the control policy may dictate operation of only two hours by any single operator, that a single operator can only operate the controlled machine 104 for six hours, etc.

If the bio-chemical control system 102 determines that the machine policy has been violated in block 606, the method 600 advances to block 608 in which the bio-chemical control system 102 causes a reactant bio-chemical agent to be dispensed at the controlled machine 104. The reactant bio-chemical agent may react harshly with the bio-chemical agent applied to the operator to cause irritation to the operator or be otherwise unpleasant so as to control the behavior of the operator (e.g., force the operator to move away from the machine). Subsequently, in block 610, the bio-chemical control system 102 determines whether the machine policy has been corrected. If so, the method 600 loops back to block 604 to continue monitoring for operators. If not, the method 600 loops back to block 608 in which the reactant biochemical agent is applied again or another reactant biochemical agent is applied to escalate control of the operator. The process may be repeated with harsher reactant biochemical agents until compliance is obtained.

EXAMPLES

Illustrative examples of the devices, systems, and methods disclosed herein are provided below. An embodiment of the devices, systems, and methods may include any one or more, and any combination of, the examples described below.

Example 1 includes a system for controlling operation of a machine, the system comprising a bio-chemical delivery system to apply a bio-chemical agent to an operator of the machine; and a bio-chemical control system to control an operational characteristic of the machine based on the presence of the bio-chemical agent on the operator.

Example 2 includes the subject matter of Example 1, and wherein to apply the bio-chemical agent to the operator comprises to, at least one of, supply a pill to the operator, spray the bio-chemical agent on the operator, or inject the bio-chemical agent into the operator.

Example 3 includes the subject matter of any of Examples 1 and 2, and wherein further including a bio-chemical sensor to sense the bio-chemical agent on the operator.

Example 4 includes the subject matter of any of Examples 1-3, and wherein to control the operational characteristic of the machine comprises to detect whether the bio-chemical agent is on the operator, and control an operational characteristic of the machine in response to detection of the bio-chemical agent on the operator.

Example 5 includes the subject matter of any of Examples 1-4, and wherein to control the operational characteristic of the machine comprises to halt operation of the machine.

Example 6 includes the subject matter of any of Examples 1-5, and wherein to control the operational characteristic of the machine comprises to detect whether the bio-chemical agent is on the operator, and control an operational characteristic of the machine in response to detection that the bio-chemical agent is not on the operator.

Example 7 includes the subject matter of any of Examples 1-6, and wherein to control the operational characteristic of the machine comprises to halt operation of the machine.

Example 8 includes the subject matter of any of Examples 1-7, and wherein to the bio-chemical agent comprises a bio-chemical agent that decays over time.

Example 9 includes the subject matter of any of Examples 1-8, and wherein to control an operational characteristic of the machine comprises halting operation of a vehicle in response to detection that the bio-chemical agent is not on the operator.

Example 10 includes the subject matter of any of Examples 1-9, and wherein to control the operational characteristic of the machine comprises to control an operational characteristic of the machine based on the presence of a bio-chemical trigger generated by the bio-chemical agent in response to application of the bio-chemical agent to the operator.

Example 11 includes the subject matter of any of Examples 1-10, and wherein the bio-chemical agent comprises a bio-chemical agent configured to generate a bio-chemical trigger in response to an interaction with a drug consumed by the operator.

Example 12 includes the subject matter of any of Examples 1-11, and wherein applying the bio-chemical agent comprises applying a bio-chemical agent configured to generate a bio-chemical trigger in response to a biological characteristic of the operator.

Example 13 includes the subject matter of any of Examples 1-12, and wherein to control the operational characteristic of the machine comprises to halt operation of the machine.

Example 14 includes the subject matter of any of Examples 1-13, and wherein to control the operational characteristic of the machine comprises to detect whether the bio-chemical trigger is present, and control an operational characteristic of the machine in response to detecting that the bio-chemical trigger is present.

Example 15 includes the subject matter of any of Examples 1-14, and wherein to control the operational characteristic of the machine comprises to personalize an operation of the machine for the operator based on the presence of the bio-chemical agent.

Example 16 includes the subject matter of any of Examples 1-15, and wherein to personalize the operation of the machine comprises to modify the operation of the machine based on a preference of the operator.

Example 17 includes the subject matter of any of Examples 1-16, and wherein the bio-chemical agent comprises a bio-chemical agent configured to generate a bio-chemical agent signature in response to a biological characteristic of the operator, wherein the bio-chemical agent signature uniquely identifies the operator, and wherein to personalize the operation of the machine for the operator comprises to personalize the operation of the machine for the operator in response to detection of the presence of the bio-chemical agent signature on the operator.

Example 18 includes the subject matter of any of Examples 1-17, and wherein the biochemical control system is further to determine whether a machine policy associated with the machine has been violated by the operator, and dispense a reactant bio-chemical agent to the operator in response to a determination that the machine policy has been violated, wherein the reactant bio-chemical agent reacts with the bio-chemical agent to cause irritation to the operator.

Example 19 includes the subject matter of any of Examples 1-18, and wherein to dispense the reactant bio-chemical agent comprises to spray the reactant bio-chemical agent on the operator.

Example 20 includes the subject matter of any of Examples 1-19, and wherein the biochemical control system is further to detect the presence of the operator at the machine, wherein to control the operational characteristic of the machine comprises to control, in response to detection of the presence of the operator at the machine, the operational characteristic of the machine based on the presence of the bio-chemical agent on the operator.

Example 21 includes the subject matter of any of Examples 1-20, and wherein to detect the presence of the operator at the machine comprises to monitor a sensor associated with the machine, wherein the sensor generates sensor data indicative of the presence of the operator at the machine.

Example 22 includes a method for controlling operation of a machine, the method comprising applying, by a bio-chemical control system, a bio-chemical agent to an operator of the machine; and controlling, by the bio-chemical control system, an operational characteristic of the machine based on the presence of the bio-chemical agent on the operator.

Example 23 includes the subject matter of Example 22, and wherein applying the bio-chemical agent to the operator comprises at least one of supplying a pill to the operator, spraying the bio-chemical agent on the operator, or injecting the bio-chemical agent into the operator.

Example 24 includes the subject matter of any of Examples 22 and 23, and wherein controlling the operational characteristic of the machine comprises sensing, by a bio-chemical sensor, the bio-chemical agent on the operator.

Example 25 includes the subject matter of any of Examples 22-24, and wherein controlling the operational characteristic of the machine comprises detecting, by a bio-chemical sensor, whether the bio-chemical agent is on the operator, and controlling, by the bio-chemical control system, an operational characteristic of the machine in response to detecting that the bio-chemical agent is on the operator.

Example 26 includes the subject matter of any of Examples 22-25, and wherein controlling the operational characteristic of the machine comprises halting operation of the machine.

Example 27 includes the subject matter of any of Examples 22-26, and wherein controlling the operational characteristic of the machine comprises detecting, by a bio-chemical sensor, whether the bio-chemical agent is on the operator, and controlling, by the bio-chemical control system, an operational characteristic of the machine in response to detecting that the bio-chemical agent is not on the operator.

Example 28 includes the subject matter of any of Examples 22-27, and wherein controlling the operational characteristic of the machine comprises halting operation of the machine.

Example 29 includes the subject matter of any of Examples 22-28, and wherein applying the bio-chemical agent comprises applying a bio-chemical agent that decay over time to the operator.

Example 30 includes the subject matter of any of Examples 22-29, and wherein controlling an operational characteristic of the machine comprises halting, by the bio-chemical control system, operation of a vehicle in response to detecting that the bio-chemical agent is not on the operator.

Example 31 includes the subject matter of any of Examples 22-30, and wherein controlling the operational characteristic of the machine comprises controlling, by the bio-chemical control system, an operational characteristic of the machine based on the presence of a bio-chemical trigger generated by the bio-chemical agent in response to application of the bio-chemical agent to the operator.

Example 32 includes the subject matter of any of Examples 22-31, and wherein applying the bio-chemical agent comprises applying a bio-chemical agent configured to generate a bio-chemical trigger in response to an interaction with a drug consumed by the operator.

Example 33 includes the subject matter of any of Examples 22-32, and wherein applying the bio-chemical agent comprises applying a bio-chemical agent configured to generate a bio-chemical trigger in response to a biological characteristic of the operator.

Example 34 includes the subject matter of any of Examples 22-33, and wherein controlling the operational characteristic of the machine comprises halting operation of the machine.

Example 35 includes the subject matter of any of Examples 22-34, and wherein controlling the operational characteristic of the machine comprises detecting, by a bio-chemical sensor, whether the bio-chemical trigger is present, and controlling, by the bio-chemical control system, an operational characteristic of the machine in response to detecting that the bio-chemical trigger is present.

Example 36 includes the subject matter of any of Examples 22-35, and wherein controlling the operational characteristic of the machine comprises personalizing an operation of the machine for the operator based on the presence of the bio-chemical agent.

Example 37 includes the subject matter of any of Examples 22-36, and wherein personalizing the operation of the machine comprises modifying the operation of the machine based on a preference of the operator.

Example 38 includes the subject matter of any of Examples 22-37, and wherein applying the bio-chemical agent comprises applying a bio-chemical agent configured to generate a bio-chemical agent signature in response to a biological characteristic of the operator, wherein the bio-chemical agent signature uniquely identifies the operator, and personalizing the operation of the machine for the operator comprises personalizing the operation of the machine for the operator in response to detection of the presence of the bio-chemical agent signature on the operator.

Example 39 includes the subject matter of any of Examples 22-38, and further including determining whether a machine policy associated with the machine has been violated by the operator, and dispensing a reactant bio-chemical agent to the operator in response to a determination that the machine policy has been violated, wherein the reactant bio-chemical agent reacts with the bio-chemical agent to cause irritation to the operator.

Example 40 includes the subject matter of any of Examples 22-39, and wherein dispensing the reactant bio-chemical agent comprises spraying the reactant bio-chemical agent on the operator.

Example 41 includes the subject matter of any of Examples 22-40, and further including detecting the presence of the operator at the machine, wherein controlling the operational characteristic of the machine comprises controlling, in response to detection of the presence of the operator at the machine, the operational characteristic of the machine based on the presence of the bio-chemical agent on the operator.

Example 42 includes the subject matter of any of Examples 22-41, and wherein detecting the presence of the operator at the machine comprises monitoring a sensor associated with the machine, wherein the sensor generates sensor data indicative of the presence of the operator at the machine.

Example 43 includes one or more computer-readable storage media comprising a plurality of instructions stored thereon that, in response to execution, cause a computing device to perform the method of any of Examples 22-42.

Example 44 includes a system for controlling operation of a machine, the system comprising means for applying, by a bio-chemical control system, a bio-chemical agent to an operator of the machine; and means for controlling, by the bio-chemical control system, an operational characteristic of the machine based on the presence of the bio-chemical agent on the operator.

Example 45 includes the subject matter of Example 44, and wherein the means for applying the bio-chemical agent to the operator comprises at least one of means for supplying a pill to the operator, means for spraying the bio-chemical agent on the operator, or means for injecting the bio-chemical agent into the operator.

Example 46 includes the subject matter of any of Examples 44 and 45, and wherein the means for controlling the operational characteristic of the machine comprises means for sensing the bio-chemical agent on the operator.

Example 47 includes the subject matter of any of Examples 44-46, and wherein the means for controlling the operational characteristic of the machine comprises means for detecting whether the bio-chemical agent is on the operator, and means for controlling an operational characteristic of the machine in response to detecting that the bio-chemical agent is on the operator.

Example 48 includes the subject matter of any of Examples 44-47, and wherein the means for controlling the operational characteristic of the machine comprises means for halting operation of the machine.

Example 49 includes the subject matter of any of Examples 44-48, and wherein the means for controlling the operational characteristic of the machine comprises means for detecting whether the bio-chemical agent is on the operator, and means for controlling an operational characteristic of the machine in response to detecting that the bio-chemical agent is not on the operator.

Example 50 includes the subject matter of any of Examples 44-49, and wherein the means for controlling the operational characteristic of the machine comprises means for halting operation of the machine.

Example 51 includes the subject matter of any of Examples 44-50, and wherein the means for applying the bio-chemical agent comprises means for applying a bio-chemical agent that decay over time to the operator.

Example 52 includes the subject matter of any of Examples 44-51, and wherein the means for controlling an operational characteristic of the machine comprises means for halting operation of a vehicle in response to detecting that the bio-chemical agent is not on the operator.

Example 53 includes the subject matter of any of Examples 44-52, and wherein the means for controlling the operational characteristic of the machine comprises means for controlling an operational characteristic of the machine based on the presence of a bio-chemical trigger generated by the bio-chemical agent in response to application of the bio-chemical agent to the operator.

Example 54 includes the subject matter of any of Examples 44-53, and wherein the means for applying the bio-chemical agent comprises means for applying a bio-chemical agent configured to generate a bio-chemical trigger in response to an interaction with a drug consumed by the operator.

Example 55 includes the subject matter of any of Examples 44-54, and wherein the means for applying the bio-chemical agent comprises means for applying a bio-chemical agent configured to generate a bio-chemical trigger in response to a biological characteristic of the operator.

Example 56 includes the subject matter of any of Examples 44-55, and wherein the means for controlling the operational characteristic of the machine comprises means for halting operation of the machine.

Example 57 includes the subject matter of any of Examples 44-56, and wherein the means for controlling the operational characteristic of the machine comprises means for detecting whether the bio-chemical trigger is present, and means for controlling an operational characteristic of the machine in response to detecting that the bio-chemical trigger is present.

Example 58 includes the subject matter of any of Examples 44-57, and wherein the means for controlling the operational characteristic of the machine comprises means for personalizing an operation of the machine for the operator based on the presence of the bio-chemical agent.

Example 59 includes the subject matter of any of Examples 44-58, and wherein the means for personalizing the operation of the machine comprises means for modifying the operation of the machine based on a preference of the operator.

Example 60 includes the subject matter of any of Examples 44-59, and wherein the means for applying the bio-chemical agent comprises means for applying a bio-chemical agent configured to generate a bio-chemical agent signature in response to a biological characteristic of the operator, wherein the bio-chemical agent signature uniquely identifies the operator, and the means for personalizing the operation of the machine for the operator comprises means for personalizing the operation of the machine for the operator in response to detection of the presence of the bio-chemical agent signature on the operator.

Example 61 includes the subject matter of any of Examples 44-60, and further including means for determining whether a machine policy associated with the machine has been violated by the operator, and means for dispensing a reactant bio-chemical agent to the operator in response to a determination that the machine policy has been violated, wherein the reactant bio-chemical agent reacts with the bio-chemical agent to cause irritation to the operator.

Example 62 includes the subject matter of any of Examples 44-61, and wherein the means for dispensing the reactant bio-chemical agent comprises means for spraying the reactant bio-chemical agent on the operator.

Example 63 includes the subject matter of any of Examples 44-62, and further including means for detecting the presence of the operator at the machine, wherein the means for controlling the operational characteristic of the machine comprises means for controlling, in response to detection of the presence of the operator at the machine, the operational characteristic of the machine based on the presence of the bio-chemical agent on the operator.

Example 64 includes the subject matter of any of Examples 44-63, and wherein the means for detecting the presence of the operator at the machine comprises means for monitoring a sensor associated with the machine, wherein the sensor generates sensor data indicative of the presence of the operator at the machine.

The invention claimed is:

1. A system for controlling operation of a machine, the system comprising:
   a bio-chemical delivery system to apply a bio-chemical agent to an operator of the machine;
   a bio-chemical control system to control an operational characteristic of the machine based on the presence of the bio-chemical agent on the operator; and
   dispense a reactant bio-chemical agent to the operator in response to a determination that a machine policy associated with the machine has been violated, wherein the reactant bio-chemical agent is to react with the bio-chemical agent to cause irritation to the operator.

2. The system of claim 1, wherein to control the operational characteristic of the machine comprises to:
   detect whether the bio-chemical agent is on the operator, and
   control an operational characteristic of the machine in response to detection of the bio-chemical agent on the operator.

3. The system of claim 2, wherein to control the operational characteristic of the machine comprises to halt operation of the machine.

4. The system of claim 1, wherein to control the operational characteristic of the machine comprises to:
   detect whether the bio-chemical agent is on the operator, and
   control an operational characteristic of the machine in response to detection that the bio-chemical agent is not on the operator.

5. The system of claim 4, wherein to the bio-chemical agent comprises a bio-chemical agent that decays over time, and
   wherein to control an operational characteristic of the machine comprises to halt operation of a vehicle in response to detection that the bio-chemical agent is not on the operator.

6. The system of claim 1, wherein to control the operational characteristic of the machine comprises to control an operational characteristic of the machine based on the presence of a bio-chemical trigger generated by the bio-chemical agent in response to application of the bio-chemical agent to the operator.

7. The system of claim 1, wherein to control the operational characteristic of the machine comprises to personalize an operation of the machine for the operator based on the presence of the bio-chemical agent.

8. The system of claim 7, wherein the bio-chemical agent comprises a bio-chemical agent configured to generate a bio-chemical agent signature in response to a biological characteristic of the operator, wherein the bio-chemical agent signature uniquely identifies the operator, and
   wherein to personalize the operation of the machine for the operator comprises to personalize the operation of the machine for the operator in response to detection of the presence of the bio-chemical agent signature on the operator.

9. One or more non-transitory, computer-readable storage media comprising a plurality of instructions stored thereon that, in response to execution, cause a system to:
   apply a bio-chemical agent to an operator of the machine;
   control an operational characteristic of the machine based on the presence of the bio-chemical agent on the operator; and
   dispense a reactant bio-chemical agent to the operator in response to a determination that a machine policy associated with the machine has been violated, wherein the reactant bio-chemical agent is to react with the bio-chemical agent to cause irritation to the operator.

10. The one or more non-transitory, computer-readable storage media of claim 9, wherein to control the operational characteristic of the machine comprises to:
    detect whether the bio-chemical agent is on the operator, and
    control, an operational characteristic of the machine in response to detecting that the bio-chemical agent is on the operator.

11. The one or more non-transitory, computer-readable storage media of claim 9, wherein to control the operational characteristic of the machine comprises to:
    detect whether the bio-chemical agent is on the operator, and
    control an operational characteristic of the machine in response to detecting that the bio-chemical agent is not on the operator.

12. The one or more non-transitory, computer-readable storage media of claim 11, wherein to:
    apply the bio-chemical agent comprises to apply a bio-chemical agent that decay over time to the operator, and
    control an operational characteristic of the machine comprises to halt operation of a vehicle in response to detecting that the bio-chemical agent is not on the operator.

13. The one or more non-transitory, computer-readable storage media of claim 9, wherein to control the operational characteristic of the machine comprises to control an operational characteristic of the machine based on the presence of a bio-chemical trigger generated by the bio-chemical agent in response to application of the bio-chemical agent to the operator.

14. The one or more non-transitory, computer-readable storage media of claim 9, wherein to control the operational characteristic of the machine comprises to personalize an operation of the machine for the operator based on the presence of the bio-chemical agent.

15. The one or more non-transitory, computer-readable storage media of claim 14, wherein to:
    apply the bio-chemical agent comprises to apply a bio-chemical agent configured to generate a bio-chemical agent signature in response to a biological characteristic of the operator, wherein the bio-chemical agent signature uniquely identifies the operator, and
    personalize the operation of the machine for the operator comprises to personalize the operation of the machine for the operator in response to detection of the presence of the bio-chemical agent signature on the operator.

16. A method for controlling operation of a machine, the method comprising:
    applying, by a bio-chemical control system, a bio-chemical agent to an operator of the machine;
    controlling, by the bio-chemical control system, an operational characteristic of the machine based on the presence of the bio-chemical agent on the operator; and
    dispensing a reactant bio-chemical agent to the operator in response to a determination that a machine policy associated with the machine has been violated, wherein the reactant bio-chemical agent is to react with the bio-chemical agent to cause irritation to the operator.

17. The method of claim 16, wherein controlling the operational characteristic of the machine comprises:
    detecting, by a bio-chemical sensor, whether the bio-chemical agent is on the operator, and
    controlling, by the bio-chemical control system, an operational characteristic of the machine in response to detecting that the bio-chemical agent is on the operator.

18. The method of claim 16, wherein controlling the operational characteristic of the machine comprises:
    detecting, by a bio-chemical sensor, whether the bio-chemical agent is on the operator, and
    controlling, by the bio-chemical control system, an operational characteristic of the machine in response to detecting that the bio-chemical agent is not on the operator.

19. The method of claim 18, wherein:
    applying the bio-chemical agent comprises applying a bio-chemical agent that decay over time to the operator, and
    controlling an operational characteristic of the machine comprises halting, by the bio-chemical control system, operation of a vehicle in response to detecting that the bio-chemical agent is not on the operator.

20. The method of claim 16, wherein controlling the operational characteristic of the machine comprises controlling, by the bio-chemical control system, an operational characteristic of the machine based on the presence of a bio-chemical trigger generated by the bio-chemical agent in response to application of the bio-chemical agent to the operator.

21. The method of claim 16, wherein controlling the operational characteristic of the machine comprises personalizing an operation of the machine for the operator based on the presence of the bio-chemical agent.

22. The method of claim 21, wherein:
applying the bio-chemical agent comprises applying a bio-chemical agent configured to generate a bio-chemical agent signature in response to a biological characteristic of the operator, wherein the bio-chemical agent signature uniquely identifies the operator, and
personalizing the operation of the machine for the operator comprises personalizing the operation of the machine for the operator in response to detection of the presence of the bio-chemical agent signature on the operator.

* * * * *